United States Patent
Mancosky

(10) Patent No.: US 10,011,804 B2
(45) Date of Patent: Jul. 3, 2018

(54) METHOD OF EXTRACTING CBD, THC, AND OTHER COMPOUNDS FROM CANNABIS USING CONTROLLED CAVITATION

(71) Applicant: Hydro Dynamics, Inc., Rome, GA (US)

(72) Inventor: Douglas G. Mancosky, White, GA (US)

(73) Assignee: EcoXtraction, LLC, Lafayette, LA (US)

( * ) Notice: Subject to any disclaimer, the term of this patent is extended or adjusted under 35 U.S.C. 154(b) by 0 days.

(21) Appl. No.: 15/240,450

(22) Filed: Aug. 18, 2016

(65) Prior Publication Data
US 2017/0051231 A1 Feb. 23, 2017

Related U.S. Application Data

(60) Provisional application No. 62/208,179, filed on Aug. 21, 2015, provisional application No. 62/279,234, filed on Jan. 15, 2016.

(51) Int. Cl.
| | |
|---|---|
| *C11B 1/10* | (2006.01) |
| *C11B 1/14* | (2006.01) |
| *C11B 1/02* | (2006.01) |
| *C11B 1/04* | (2006.01) |
| *C07D 309/18* | (2006.01) |

(52) U.S. Cl.
CPC .............. *C11B 1/10* (2013.01); *C07D 309/18* (2013.01); *C11B 1/02* (2013.01); *C11B 1/04* (2013.01); *C11B 1/106* (2013.01); *C11B 1/14* (2013.01)

(58) Field of Classification Search
CPC ..... C11B 1/10; C11B 1/14; C11B 1/02; C11B 1/106; C11B 1/04; C07D 309/18
See application file for complete search history.

(56) References Cited

U.S. PATENT DOCUMENTS

| | | |
|---|---|---|
| 1,758,207 A | 5/1930 | Walker |
| 2,283,244 A | 5/1942 | Walker |
| 3,211,850 A | 10/1965 | Toepfer |
| 4,213,332 A | 7/1980 | Bonomo et al. |
| 4,626,319 A | 12/1986 | Kruger et al. |
| 4,864,872 A | 9/1989 | Stahl |
| 5,385,298 A | 1/1995 | Griggs |
| 5,571,975 A | 11/1996 | Smith, Jr. et al. |
| 5,957,122 A | 9/1999 | Griggs |
| 6,221,206 B1 | 4/2001 | Bokstrom et al. |
| 6,627,784 B2 | 9/2003 | Hudson et al. |
| 6,700,014 B2 * | 3/2004 | Jerz .......................... C07J 63/00 562/498 |
| 7,271,304 B2 | 9/2007 | Du Toit |
| 7,360,755 B2 | 4/2008 | Hudson et al. |
| 7,507,014 B1 | 3/2009 | League et al. |
| 7,867,422 B2 | 1/2011 | Nelson et al. |
| 8,445,034 B1 * | 5/2013 | Coles, Jr. ................ A61K 31/05 424/725 |
| 8,609,115 B2 * | 12/2013 | Hassan ............... B01F 7/00766 424/400 |
| 2004/0103783 A1 | 6/2004 | Hudson et al. |
| 2004/0232006 A1 | 11/2004 | Kazem |
| 2005/0042129 A1 | 2/2005 | Kazem |
| 2005/0150618 A1 | 7/2005 | Kazem et al. |
| 2008/0272056 A1 | 11/2008 | Kazem |
| 2014/0330030 A1 * | 11/2014 | Ferri ..................... C07C 37/004 549/389 |
| 2015/0328604 A1 | 11/2015 | Smith |
| 2016/0096122 A1 | 4/2016 | Smith et al. |
| 2016/0228787 A1 * | 8/2016 | Payack ................... B01D 3/10 |

FOREIGN PATENT DOCUMENTS

| | | |
|---|---|---|
| EP | 0 610 914 | 8/1994 |
| JP | 55-102491 | 8/1980 |
| JP | 60-226594 | 11/1985 |
| JP | 62-213895 | 9/1987 |
| WO | WO 2007/030452 | 3/2007 |
| WO | WO 2011/084392 | 7/2011 |

OTHER PUBLICATIONS

Alexandru, L., "Ultrasound-assisted extraction of clove buds using batch-and flow-reactors: A comparative study on a pilot scale." Innovative Food Science & Emerging Technologies 20 (2013): 167-172.*
Vinatoru, M., "An overview of the ultrasonically assisted extraction of bioactive principles from herbs." Ultrasonics sonochemistry 8.3 (2001): 303-313.*
Carvalho, I.S., "Evaluation of oil composition of some crops suitable for human nutrition." Industrial Crops and Products 24.1 (2006): 75-78.*
Mölleken, H., "Cannabinoids in seed extracts of Cannabis sativa cultivars." J. Int. Hemp Assoc 4.2 (1997): 76-79.*
Wakeman, R. J., "Extraction, Liquid-Solid." Kirk-Othmer Encyclopedia of Chemical Technology (2000).*
Diniz, J.M.B.F., "Hornification—its origin and interpretation in wood pulps." Wood Science and Technology 37.6 (2004): 489-494.*

* cited by examiner

*Primary Examiner* — John M Mauro
(74) *Attorney, Agent, or Firm* — Jones Walker LLP

(57) ABSTRACT

A method of extracting CBD, THC, desirable oils, and other compounds from the cannabis plant includes drying the plant, grinding or chopping the plant, mixing the resulting pieces of the plant with a fluid to form a mixture, circulating the mixture through a controlled cavitation reactor to liberate CBD, THC, desirable oils, and other compounds from the pieces, and separating the liberated CBD, THC, desirable oils, and other compounds from the fluid. The method may be used as an adjunct to or in combination with traditional extraction techniques such as leaching to increase yields.

11 Claims, 2 Drawing Sheets

METHOD OF EXTRACTING CBD, THC, AND OTHER COMPOUNDS FROM CANNABIS USING CONTROLLED CAVITATION

REFERENCE TO RELATED APPLICATION

Priority is hereby claimed to the filing date of U.S. provisional patent application 62/208,179 filed on Aug. 21, 2015 and to the filing date of U.S. provisional patent application 62/279,234 filed on Jan. 15, 2016. The content of these two provisional patent applications is hereby incorporated by reference.

TECHNICAL FIELD

The invention exemplified herein with representative embodiments generally relates to extraction of compounds from biomass and more specifically to the extraction of cannabinoids (CBD), Tetrahydrocannabinol (THC), desirable oils, and other compounds from the cannabis plant.

BACKGROUND

Cannabis legalization in several jurisdictions has led to strong demand for products made from the oils and chemical compounds that can be extracted from Cannabis (referred to herein as "extracts") and used by individuals without smoking the plant itself. For example, demand has grown in the areas of Pharmaceuticals commonly referred to as "medical marijuana," and in nutritional supplements, edible products, and vaporizer fluids to name a few. Cannabis extracts are traditionally made by exposing cannabis plants to carbon dioxide, butane, propane, alcohol, glycerin, and/or other solvents in a vessel or mixer to leach the extracts from cannabis plants (a process referred to as leaching. Ultrasound also has been used in an attempt to liberate the extracts from the cannabis plant. These and other traditional techniques often suffer from issues such as low yield, high cost, safety issues, and/or contaminants that adversely affect the flavor or efficacy of the resulting extracts.

A need exists for a method of extracting CBD, THC, desirable oils, and other compounds from cannabis that addresses and resolves the problems and shortcomings of prior art leaching and other techniques, that is more efficient at extracting such compounds, that can be selective, and that does not introduce unwanted contaminants into the resulting extracts. There is a further need for a method and apparatus for maximizing the generally low extract yields that are characteristic of prior art extraction techniques. It is to the provision of such a method that the present invention is primarily directed.

SUMMARY

It has been shown that the pressure fluctuations induced by cavitation events can enhance extraction of diverse natural substrates, substances, and compounds from a range of lignocellulosic material including, for example, wood, corn, hops, and others. Certain of our issued patents and pending patent applications, including U.S. Pat. No. 8,430, 968, disclose various techniques for extracting compounds from lignocellulosic materials using controlled cavitation. Those patents and patent applications are hereby incorporated by reference. The inventors have discovered a method and apparatus for applying controlled cavitation technology to the extraction of CBD, THC, desirable oils, and other compounds from the cannabis plant. They also have discovered a method and apparatus for enhancing the effectiveness of such extraction methodology compared to the traditionally low yield prior art extraction techniques.

Briefly described, the method of the invention comprises drying the cannabis plant; optionally separating various parts of the plant such as leaves, stems, and seed; chopping or grinding the plant parts together or separately into small pieces; mixing the pieces with a fluid that may or may not contain solvents; and passing the mixture through a controlled cavitation zone. Within the cavitation zone, high intensity shock waves and the corresponding highly energetic pressure variations penetrate the cannabis pieces within the mixture. This, in turn, liberates CBD, THC, oils, and other compounds entrapped within the pieces through a number of processes. Such processes may include, for example, forcing fluid into and out of the pieces to mix with trapped oils and substances, lysis of hard-to-penetrate cells to liberate compounds trapped therein, and reversal of hornification due to drying. The result is higher yield, higher efficiency, and lower cost extraction. As an enhancement, the method and apparatus of the invention may be employed before or after traditional extraction techniques to increase the efficiency and yields produced by those techniques.

An apparatus for carrying out the method comprises a housing containing a rotor with cavitation inducing structures on its surface. A cavitation zone is defined between the surface having cavitation inducing structures and the wall of the housing. The rotor is rotated within the housing and the mixture of fluid and entrained cannabis pieces is pumped through the housing in such a way that the mixture passes through the cavitation zone. The cavitation inducing structures on the rotor cause highly energetic and continuous cavitation events within the fluid of the mixture, which induce high energy shock waves that travel through the mixture.

As a result of the shock waves, the cannabis plant pieces are exposed to extreme, rapid, and highly energetic pressure variations that force the fluid of the mixture into and out of the cannabis pieces. The cannabis pieces also are subjected to the high energies of the shock waves. This activity along with other processes such as lysis of cell walls caused by the energy of the shock waves, dislodges CBD, THC and other oils and compounds trapped in the lignin, trichrome, cells, and pours of the cannabis. These compounds become dissolved in the fluid of the mixture and can be separated from the fluid later through known separation techniques.

Accordingly, a method of extracting CBD, THC and other compounds from cannabis is now provided that is highly efficient, extracts more of the compounds than traditional extraction techniques, does so at a lower cost, can be controlled for selective extraction of particular compounds, and is readily scalable to virtually any commercial production rate. The method and apparatus also can be used to enhance traditional extraction techniques such as leaching to increase and maximize yields. These and other aspects, features, and advantages of the invention will be better understood upon review of the detailed description presented below taken in conjunction with the attached drawing figures, which are briefly described as follows.

DETAILED DESCRIPTION

Figure 1:
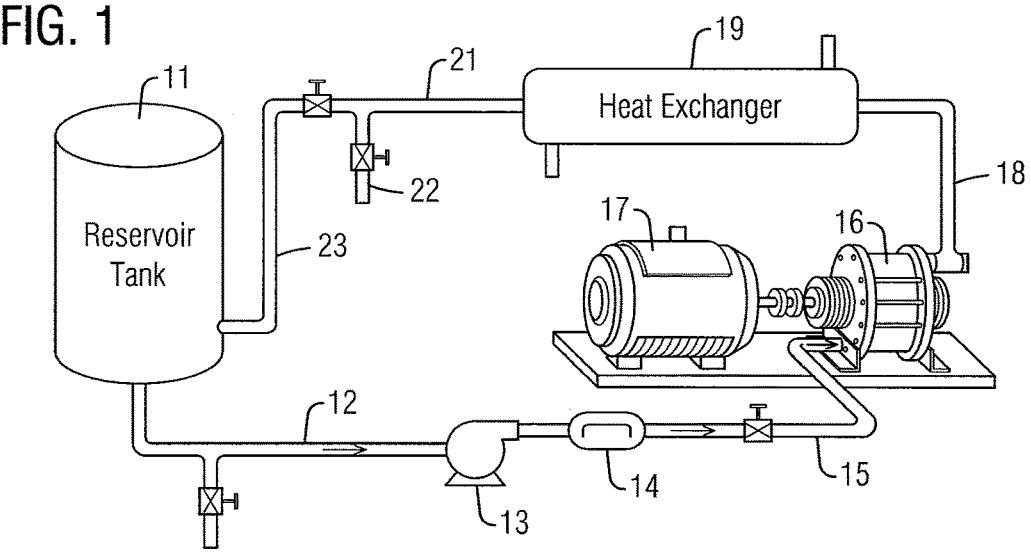
FIG. 1 is an illustration of one embodiment of a controlled cavitation apparatus usable for extracting CBD, THC, desirable oils, and other compounds from cannabis according to the methodology of the invention.

Reference will now be made in more detail to the accompanying drawing figures, wherein various reference numerals and labels identify the various parts of the apparatus. Referring to FIG. 1, an apparatus for carrying out the methodology of the invention includes, in one illustrative embodiment, a reservoir tank 11 for holding a mixture of a fluid and ground or chopped pieces of the cannabis plant. The fluid may be water, a solvent, a surfactant, a reactant, an acid, a base, combinations thereof, or any other fluid effective to liberate CBD, THC and other oils and products from the cannabis plant. Water is a preferred fluid. A pump 13 communicates with the reservoir tank 11 through a conduit 12 and is configured to pump the mixture from the reservoir tank 11, through a flow meter 14, through conduit 15, to and through controlled cavitation device 16.

The controlled cavitation device 16 includes a housing within which a rotor (not visible but disclosed in the incorporated references) that can be rotated at a preselected and controllable speed by motor 17. The rotor has cavitation inducing structures such as arrays of bores formed in its peripheral cylindrical surface. A cavitation zone having a predetermined dimension is defined between the peripheral surface of the rotor bearing the cavitation inducing structures and an interior surface of the housing. The flow path of mixture moving through the controlled cavitation device 16 moves the mixture through the cavitation zone.

Rotation of the rotor within the controlled cavitation device 16 as the mixture is pumped through the cavitation zone induces highly energetic cavitation events in the mixture. These cavitation events induce highly energetic shock waves and corresponding highly intense and rapid pressure fluctuations that propagate through the mixture within the cavitation zone. As detailed below, this environment liberates CBD, THC and other oils and compounds from the cannabis pieces within the mixture and these compounds become dissolved or entrained within the fluid of the mixture. Upon leaving the controlled cavitation device 16, the mixture flows through conduit 18, through a heat exchanger 19 for removing heat generated by the cavitation process, and through conduits 21 and 23 back to the reservoir tank 11. A sample line 22 may be provided for extracting samples of the treated fluid for testing.

The mixture may be circulated through the controlled cavitation device 16 numerous times until the extraction of CBD, THC and other oils and compounds is maximized. Alternatively, single pass treatment may well be acceptable in many instances. Subsequently, the remaining lignin from the cannabis pieces is separated from the mixture and the CBD, THC and other oils and compounds, now dissolved or entrained within the fluid of the mixture, can be separated from the fluid of the mixture through standard techniques. The efficiency yield of extraction in the present invention is substantially greater than prior art extraction techniques and methods, the cost is lower, and the present invention may be scaled up easily to virtually any commercial production rate. The invention can thus be used to extract desirable compounds such as CBD, THC and oils for medicinal or other legal uses from cannabis on a commercial scale.

In a preferred exemplary methodology, cannabis plant is first dried. After drying, the cannabis plant can be coarsely chopped or finely ground into relatively small pieces. Various elements of the plant such as the leaves, stems, and seeds can be separated for independent treatment, or the elements may be left in the mix and treated together. The ground plant pieces are mixed with water to form a mixture. Solvents other than water can be added to the mixture if desired, but this is not considered to be a requirement or limitation of the invention. Such solvents, if added, can include, for example, carbon dioxide, alcohols, glycerin, propane, and/or butane among others. In one embodiment, the preferred solvent is simply water, which eliminates the problem with prior art techniques wherein residual contaminates from harsher solvents may remain in the extracted product.

The mixture can be circulated through the apparatus at various rates and for varying periods of time, through varying circulation cycles, and with varying temperatures, solvents, and cavitation intensities to alter the amount and type of compounds extracted. For example, a more easily dislodged compound may be extracted using less energetic cavitation, leaving less easily dislodged compounds for later extraction with more energetic cavitation. The time that the mixture is exposed to cavitation can be varied from a few minutes to many hours to obtain the desired result. The heat exchanger 19 may or may not be incorporated into the circuit, but generally is desirable for longer circulation times to dissipate heat build-up caused by the energy imparted to the mixture by cavitation. Internal clearances within the controlled cavitation device 16 may be adjusted or selected to handle different size pieces of the cannabis plant entrained within the flow of the mixture. Surface area of the ground pieces is an independent variable.

The method of this invention offers many advantages over somewhat similar extraction technologies such as ultrasound. Ultrasound is typically difficult to scale-up and replicate laboratory results on a commercial scale. The use of controlled cavitation according to the present invention can provide a better result at nearly any commercial volume. Cavitation also produces more energetic shock waves than ultrasound in the sense that higher energy pressure variations are generated by the cavitation events. This may also result in faster and higher yield. Finally, ultrasound and other cavitation technologies rely on small clearances or high shear that are not conducive to extraction of compounds from natural substrates such as plant material. Extraction through controlled cavitation according to the present invention can easily incorporate plant and other lignocellulosic material because of its inherent low shear and relatively large clearances within the cavitation zone.

In addition to the cavitation induced pressure fluctuations forcing solvent into cannabis pieces to liberate an entrapped compound, these pressure fluctuations are also capable of lysis (breaking down the membranes) of pressurized bodies like cells. These cells often harbor desirable compounds that are otherwise difficult to liberate due to the resiliency of the cell membranes. The lysis coupled with cavitation provides increased yield and selectivity. Exposing cannabis pieces to cavitation according to the present invention also can reverse hornification. Hornification occurs when the pore structure of the dried cannabis plant dries and bonds to itself thereby limiting future extraction from the natural capillary system of the plant. The highly energetic cavitation induced pressure fluctuations and shock waves of the present invention forces solvent into these dried structures and reopens them to near their original configuration before the plant was dried, again increasing yield.

The intensity of the cavitation and therefore the energy of the shock waves and pressure variations can be controlled by, for example, varying the rate of rotation of the rotor, so that a desired result is selectively achieved without causing other less desirable results. For example, many of the compounds of interest are contained in a plant structure called the trichrome. By controlling the rotation rate of the rotor to obtain a predetermined cavitation intensity, the trichrome can simple be knocked off the plant material for later extraction. A different cavitation intensity can be selected to burst the trichrome to liberate the compounds therein. The intensity can be selected to burst the cells in the main body of the plant, which releases smaller amounts of desired compounds, but also may release some undesirable compounds. Multiple passes through the controlled cavitation device setting different cavitation energies each pass may be used to, for example, liberate compounds from plant structures that yield the purist compounds in initial passes while liberating compounds from harder-to-extract-from structures or structures that also yield undesirable compounds in later passes.

Figure 2:
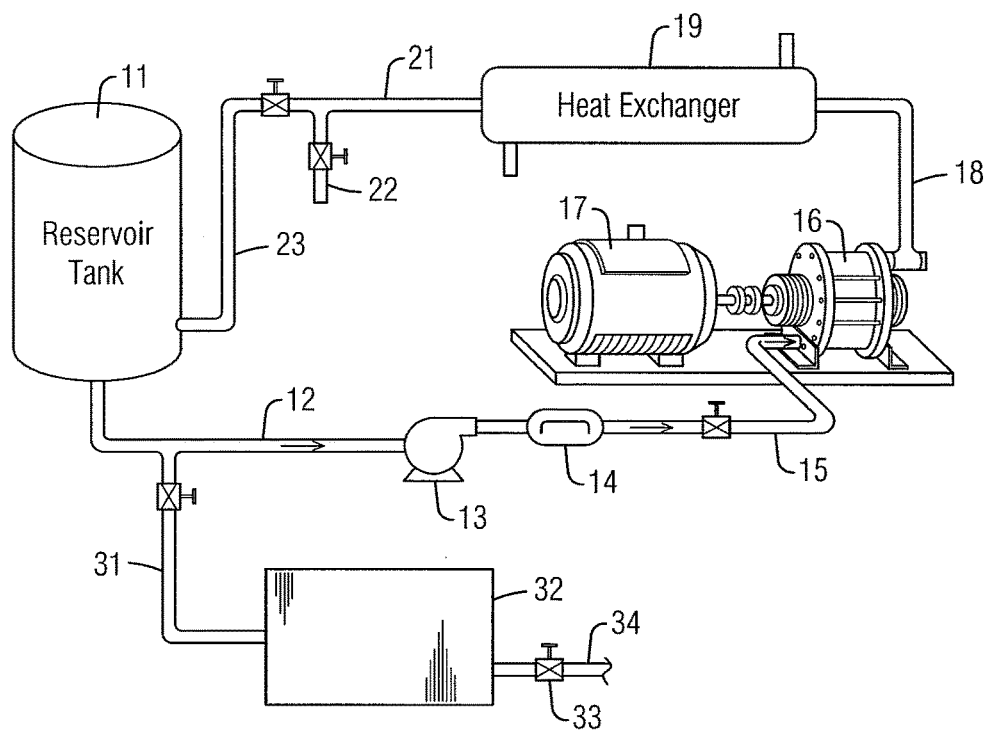
FIG. 2 is an illustration of a controlled cavitation apparatus used as a pre-extractor in conjunction with a traditional extraction technique to enhance the efficiency and yield of the traditional extraction technique.

The invention also can be used as an enhancement to more traditional lower-yield extraction techniques to improve significantly the efficiency and yield of such techniques. In FIG. 2, a traditional extraction system 32, such as a leaching system for example, is configured to extract CBD, THC and other substances from cannabis in a traditional manner. Such systems are inherently inefficient in that much of the CBD, THC and other substances are not extracted and are left trapped in the plant material. The traditional system has an outlet 34 and a valve 33 for removing fluid that contains the extracted compounds when the treatment is complete. In this embodiment, the cavitation extraction system of FIG. 1 is arranged upstream of the traditional extraction system in a pre-treatment configuration. Water or solvent containing CBD, THC and perhaps other compounds extracted in the cavitation extraction system can be delivered to the traditional extraction system 32 through conduit 31 for additional treatment. The initial pre-treatment in the cavitation extractor may serve to open pores, penetrate cell walls, and open capillaries in the cannabis plant as it extracts some of the CBD, THC and other compounds. This, in turn, can enhance the efficiency of the traditional extraction process 32 by allowing the leaching solvent to penetrate the opened pores, breached cell walls, and opened capillaries generated in the pre-treatment process.

Figure 3:
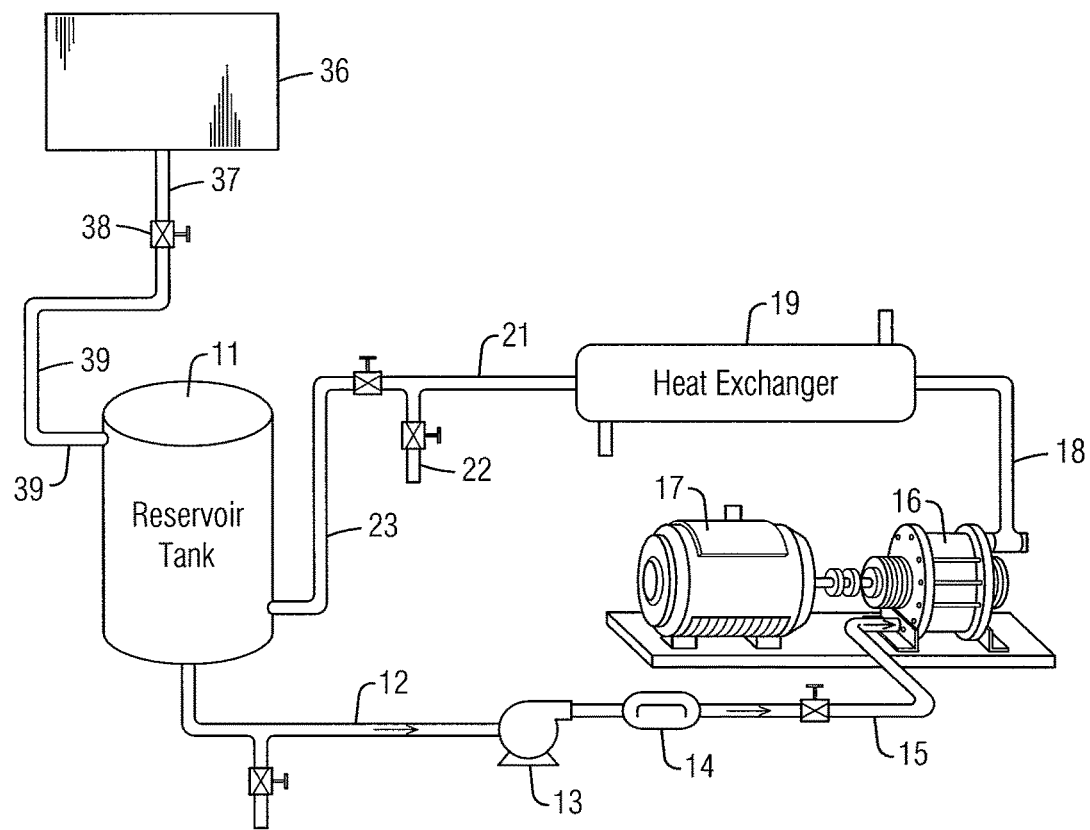
FIG. 3 is an illustration of a controlled cavitation apparatus used as a post-extractor in conjunction with a traditional extraction technique to enhance the efficiency and yield of the traditional extraction technique.

FIG. 3 illustrates a process in which the cannabis plant is initially treated in a traditional extraction system 36 and then delivered through conduit 37, valve 38, and pipe 39 to the cavitation extraction apparatus of FIG. 1. In this case, the cavitation extraction system is configured as a post-treatment system. After the traditional extraction system as extracted the CBD, THC and other compounds that it is capable of extracting, the resulting effluent is passed through the cavitation extractor to remove remaining CBD, THC and other compounds from the cannabis plant material. Since much of the CBD, THC and other compounds are extracted in the traditional extraction system 36, it should take less time to extract remaining CBD, THC and other compounds using the cavitation extraction technique of the present invention. The ultimate result is that the compounds become dissolved or entrained in the fluid and can be separated later through known techniques.

The invention has been described above in terms and within the context of preferred embodiments and methodologies considered by the inventor to represent the best modes of carrying out the invention. It will be understood, however, that the invention certainly is not limited to the illustrated embodiments and methodologies. A wide range of additions, deletions, and modifications, both subtle and gross, might well be made to the illustrated embodiments by the skilled artisan without departing from the spirit of scope of the invention, which is delineated only by the claims. For example, while it is preferred to dry the cannabis plant and to chop the dried plant into small pieces, this is not necessarily a limitation of the invention. It is possible to carry out the methodology of the invention with undried cannabis plant material that is either chopped into pieces or left as a whole plant. The claims should not be construed to exclude carrying out the methodology with undried plant material.

What is claimed is:

1. A method of extracting oils from the cannabis plant comprising the steps of:
    (a) drying the cannabis plant;
    (b) chopping or grinding the dried cannabis plant into pieces;
    (c) combining the pieces of cannabis plant with a fluid to form a mixture;
    (d) passing the mixture through a cavitation zone;
    (e) causing cavitation events in the fluid that produce shock waves and pressure variations in the cavitation zone, the cavitation zone being defined between the outer peripheral surface of a rotor and an interior surface of a housing within which the rotor is rotatably mounted, the rotor having cavitation inducing structures on its outer peripheral surface, and wherein the step of causing cavitation events comprises rotating the rotor within the housing as the mixture passes through the cavitation zone;
    (f) as a result of step (e), liberating oils from the pieces of the cannabis plant, the liberated oils becoming entrained within the fluid; and
    (g) separating the oils from the fluid;
    where in step (e), the shock waves and pressure variations are controlled by varying the rotation rate of the rotor to reverse hornification caused by step (a).

2. The method of extracting oils from the cannabis plant as claimed in claim 1 wherein step (f) comprises liberating CBD from the pieces of the cannabis plant.

3. The method of extracting oils from the cannabis plant as claimed in claim 1 where in step (c), the fluid comprises water.

4. The method of extracting oils from the cannabis plant as claimed in claim 1 where in step (c), the fluid comprises a solvent.

5. The method of extracting oils from the cannabis plant as claimed in claim 4 wherein the solvent is selected from a group consisting essentially of carbon dioxide, alcohol, glycerin, propane, butane, and mixtures thereof.

6. The method of extracting oils from the cannabis plant as claimed in claim 5 wherein the solvent is mixed with water to form the fluid.

7. The method of extracting oils from the cannabis plant as claimed in claim 1 further comprising the step of subjecting the mixture to a non-cavitation based extraction process prior to step (d).

8. The method of extracting oils from the cannabis plant as claimed in claim 7 wherein the non-cavitation based extraction process comprises leaching.

9. The method of extracting oils from the cannabis plant as claimed in claim 1 further comprising the step of subjecting the mixture to a non-cavitation based extraction process following step (e).

10. The method of extracting oils from the cannabis plant as claimed in claim 9 wherein the non-cavitation based extraction process comprises leaching.

11. The method of extracting oils from the cannabis plant as claimed in claim 1 where in step (e), the shock waves and pressure variations are controlled by adjusting the rotation rate of the rotor to break down membranes of pressurized bodies in the pieces of the cannabis plant to release oils from the pressurized bodies.

\* \* \* \* \*